US00PP22978P2

(12) United States Plant Patent
Cole, III

(10) Patent No.: US PP22,978 P2
(45) Date of Patent: Aug. 21, 2012

(54) BOXWOOD PLANT NAMED 'HIGHLANDER'

(50) Latin Name: *Buxus sempervirens*
Varietal Denomination: cv. Highlander

(75) Inventor: Norman H. Cole, III, Pipestrem, WV (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 13/067,770

(22) Filed: Jun. 24, 2011

(51) Int. Cl.
*A01H 5/00* (2006.01)

(52) U.S. Cl. ..... Plt./226
(58) Field of Classification Search ..... Plt./226
See application file for complete search history.

(56) References Cited

OTHER PUBLICATIONS

Buxus 'Highlander'. Retrieved from the Internet at <http://www.conard-pyle.com/index.cfm?fuseaction=spplants.plantDetail&plant_id=1855> 2012, retrieved on Feb. 9, 2012, 2 pages.*

* cited by examiner

*Primary Examiner* — June Hwu
*Assistant Examiner* — Louanne Krawczewicz Myers
(74) *Attorney, Agent, or Firm* — Buchanan Ingersoll & Rooney PC

(57) ABSTRACT

A new and distinct Boxwood plant is provided that originated as a mutation of unknown causation while growing among a block of vegetatively propagated *Buxus sempervirens* plants in a plant nursery. The new cultivar readily can be distinguished from other plants of the *Buxus sempervirens* species in view of its more rapid growth rate and upright pyramidal habit. Attractive deep green foliage is formed which well retains its coloration throughout the year in the absence of any substantial color change during the winter. Excellent winter hardiness to at least U.S.D.A. Hardiness Zone No. 5 is displayed. The plant is well suited for consistently providing attractive ornamentation in the landscape.

1 Drawing Sheet

Botanical/commercial classification: *Buxus sempervirens*/Boxwood Plant.

Varietal denomination: cv. Highlander.

SUMMARY OF THE INVENTION

The new Boxwood plant of the present invention is a mutation of unknown causation that was discovered in a plant nursery at Pipestem, W. Va., U.S.A., while growing among a block of vegetatively propagated *Buxus sempervirens* plants (non-patented in the United States). The parentage of the new plant is unknown; however, it is believed to be of the same species. I was initially attracted to the plant in view of its distinctive appearance primarily attributable to its attractive dark green foliage, and its rapid and upright pyramidal growth habit. Had I not discovered and preserved this new plant, it would have been lost to mankind.

The new cultivar has been carefully preserved and has been evaluated to confirm that its characteristics are reliably expressed.

It has been found that the new Boxwood plant of the present invention displays the following combination of characteristics:

(a) forms a dense and upright pyramidal growth habit,
(b) forms attractive dark green foliage throughout the year in the absence of any substantial color change during the winter,
(c) exhibits excellent winter hardiness to at least U.S.D.A. Hardiness Zone No. 5,
(d) generally exhibits a more rapid growth rate than the *Buxus sempervirens* species, and (e) is well suited for providing attractive ornamentation in the landscape.

The new evergreen cultivar of the present invention well retains its attractive appearance throughout the year. The dark green coloration of the foliage is well maintained even during the winter, unlike many previously available Boxwood cultivars which tend to assume a brownish-green foliage coloration during the winter. The new cultivar also exhibits good resistance to winter burn. The hardiness of the new cultivar during observations to date has been found to be at least equal to or to exceed most previously known Boxwood cultivars that are known for their superior hardiness.

The new cultivar of the present invention can be grown to advantage as attractive ornamentation in the landscape, and is particularly well suited for use in the formation of hedges or foundation plantings. The new plant has been found to perform well in the sun as well as in the shade while growing in many soil types, including those which contain clay.

The new plant of the present invention can be readily distinguished from other plants of the *Buxus sempervirens* species in view of its much more rapid growth rate and upright pyramidal habit.

Asexual reproduction of the new plant by the use of cuttings has been carried out at Pipestem, W. Va., U.S.A., and West Grove, Pa., U.S.A. Such propagation has confirmed that the unique combination of characteristics of the new cultivar has been stably established and is well transmitted to successive generations. The new cultivar asexually reproduces in a true-to-type manner.

The new cultivar has been named 'Highlander'.

BRIEF DESCRIPTION OF THE PHOTOGRAPH

The accompanying photograph shows as nearly true as it is reasonably possible to make the same in a color illustration of this character, a typical specimen of the new variety. A mature plant at an age of approximately eight years is shown while growing outdoors at Pipestem, W. Va., U.S.A. The upright pyramidal growth habit, dense growth, and attractive dark green foliage are illustrated.

DETAILED DESCRIPTION

The following is a detailed description of the new plant of the present invention which generally was prepared while observing two-year-old plants growing in containers outdoors during May 2011 at West Grove, Pa., U.S.A. Color terminology is in accordance with The R.H.S. Colour Chart of The Royal Horticultural Society, London, England (1995 or equivalent), except when general color terms which are to be accorded their customary dictionary significance are used.

Type: Hardy broad-leafed evergreen shrub for garden decoration and general landscape usage.

Plant:

*Growth habit*.—Fast growing, upright, pyramidal, dense.

*Growth rate*.—Rapid growth, on average approximately 20 to 24 inches of new growth has been observed per year; however, on some occasions up to 30 inches of new growth has been observed per year.

*Height*.—Approximately five feet at an age of five years.

*Width*.—Approximately three feet at an age of five years.

*Side branches*.—Diameter: commonly approximately 2 mm on average. Texture: smooth to slightly hirsute and rough in some areas. Color: primarily Greyed-Orange Group 165C with some striations of Yellow-Green Group 144A.

*Main branches*.—Diameter: commonly approximately 5 mm on average. Texture: somewhat rough. Color: Grey-Brown Group 199D. Length: for a two-year-old plant lateral side branches commonly are approximately 29 cm on average and main branches are approximately 61 cm on average.

*Roots*.—Description: highly branched and dense. Color (new growth): White Group 155A. Color (mature): Greyed-Yellow Group 160D.

Foliage:

*Arrangement*.—Decussate.

*Juvenile foliage*.—Length: commonly approximately 1.8 cm on average. Width: commonly approximately 1 cm on average. Shape: ovate. Apex: notched. Margin: entire. Color of upper surface: Green Group 143A. Color of under surface: Green Group 143C. Fragrance: typical boxwood scent.

*Mature foliage*.—Length: commonly approximately 2.5 cm on average. Width: commonly approximately 1.3 cm on average. Shape: ovate. Apex: slightly notched. Base: cuneate. Texture: glossy on the upper surface, and smooth with a pronounced midrib on the under surface. Venation pattern: pinnate. Margin: entire. Color of upper surface: commonly Green Group 137A. Color of lower surface: Yellow-Green Group 144A with striations of Yellow-Green Group 144C towards the center of the leaf. Venation color: on the upper surface Yellow-Green Group 144A and on the under surface Yellow-Green Group 144C. Winter foliage: commonly assumes a shiny aspect on the upper surface and a color blend of Yellow-Green Group 147A and Yellow-Green Group 152A. Fragrance: typical boxwood scent.

*Petioles*.—Length: approximately 2 mm on average when mature. Diameter: approximately 1 mm on average when mature. Texture: smooth when mature. Color: Yellow-Green Group 144B.

Inflorescence:

*Time*.—March-April at West Grove, Pa., U.S.A. Type: apetalous, monoecious. Arrangement: opposite at the leaf basal attachment. Number per inflorescence: approximately 10 male flowers surround a centrally located single female flower. Pistil number: 3. Pistil length: approximately 2 mm. Pistil color: Green Group 143C. Stigma shape: bi-lobed. Stigma size: approximately 1 mm in diameter. Stigma color: Yellow-Green Group 145C. Ovary length: approximately 2 mm. Ovary diameter: approximately 3 mm. Ovary color: Green Group 143A. Stamen number: approximately 4 per male flower. Stamen color: White Group 155C. Anther shape: bi-lobed ovate. Anther color: Yellow Group 9D. Pollen: present in abundance and light yellow in coloration. Fragrance: no flower fragrance observed. Fruit and seeds: none encountered during observations to date.

Development:

*Hardiness*.—To at least U.S.D.A. Hardiness Zone No. 5. Grows well in U.S.D.A. Hardiness Zone Nos. 5 to 9.

*Disease resistance*.—No disease problems have been observed during observations to date.

*Insect tolerance*.—No insect damage has been observed during observations to date.

Plants of the new 'Highlander' variety have not been observed under all possible environmental conditions to date. Accordingly, it is possible that the phenotypic expression may vary somewhat with changes in light intensity and duration, cultural practices, and other environmental conditions.

I claim:

1. A new and distinct Boxwood plant possessing the following characteristics:

(a) forms a dense and upright pyramidal growth habit, (b) forms attractive dark green foliage throughout the year in the absence of any substantial color change during the winter, (c) exhibits excellent winter hardiness to at least U.S.D.A. Hardiness Zone No. 5, (d) generally exhibits a more rapid growth rate than the *Buxus sempervirens* species, and (e) is well suited for providing attractive ornamentation in the landscape;

substantially as illustrated and described.

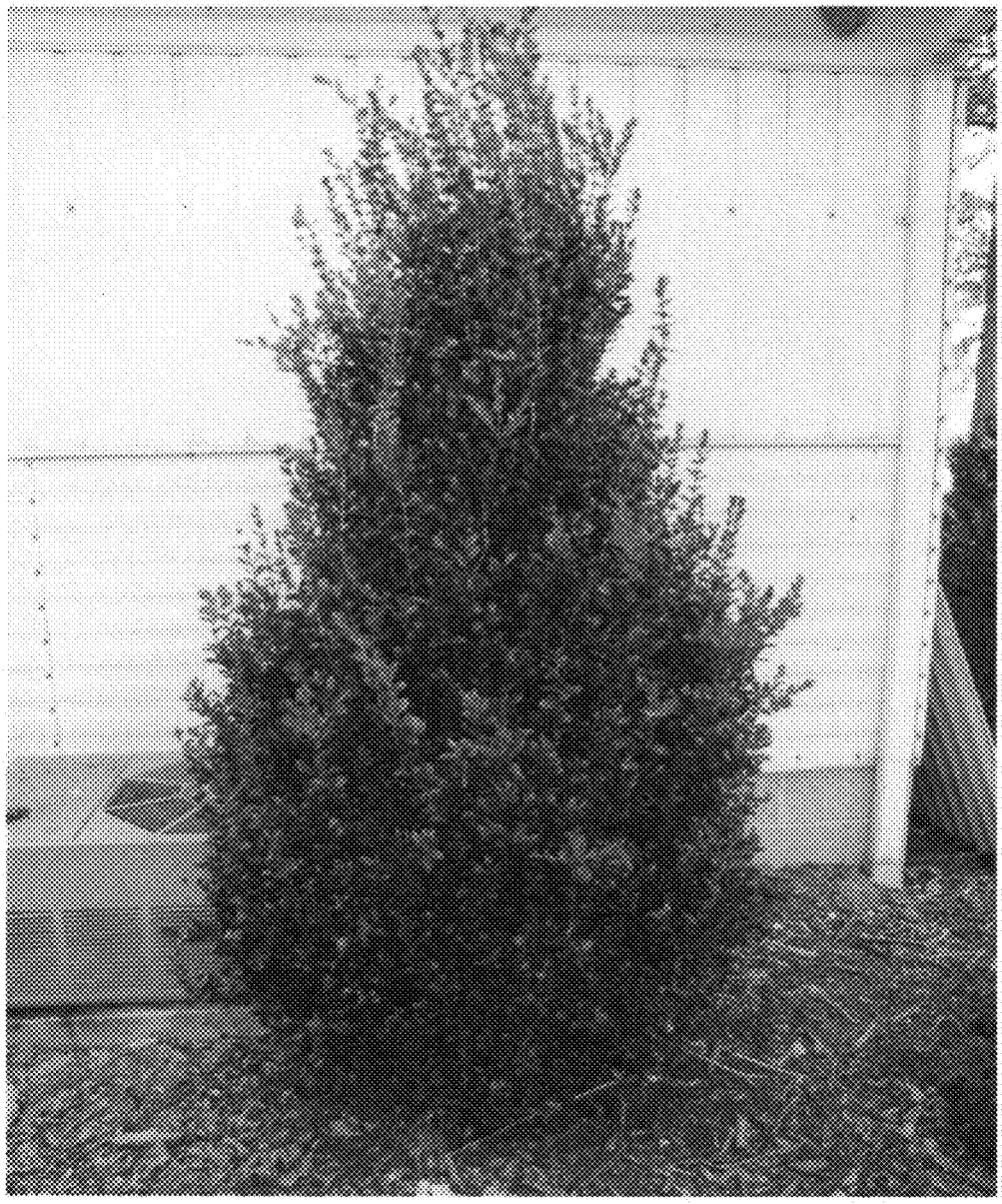

* * * * *